(12) United States Patent
Hartlep et al.

(10) Patent No.: US 7,715,902 B2
(45) Date of Patent: May 11, 2010

(54) DETERMINING DISTRIBUTION FOR PLANNING AN INFUSION

(75) Inventors: Andreas Hartlep, München (DE);
Christoph Pedain, München (DE);
Raghu Raghavan, Baltimore, MD (US);
Martin Brady, Baltimore, MD (US)

(73) Assignee: BrainLAB AG, Feldkirchen (DE)

( * ) Notice: Subject to any disclaimer, the term of this patent is extended or adjusted under 35 U.S.C. 154(b) by 938 days.

(21) Appl. No.: 10/661,827

(22) Filed: Sep. 12, 2003

(65) Prior Publication Data

US 2004/0138551 A1      Jul. 15, 2004

Related U.S. Application Data

(60) Provisional application No. 60/437,368, filed on Dec. 31, 2002.

(30) Foreign Application Priority Data

Sep. 12, 2002   (EP) .................................. 02020475

(51) Int. Cl.
*A61B 6/00*      (2006.01)
(52) U.S. Cl. ....................... 600/431; 382/128; 382/131; 600/407; 600/419
(58) Field of Classification Search ................ 606/427, 606/130, 891, 434; 600/420, 410, 412; 604/43, 604/49, 50, 51, 93, 891.1
See application file for complete search history.

(56) References Cited

U.S. PATENT DOCUMENTS

| | | |
|---|---|---|
| 5,205,289 A | 4/1993 | Hardy et al. |
| 5,583,902 A | 12/1996 | Bae |
| 5,735,814 A * | 4/1998 | Elsberry et al. ............... 604/43 |
| 6,026,316 A * | 2/2000 | Kucharczyk et al. ........ 600/420 |
| 6,061,587 A | 5/2000 | Kucharczyk et al. |
| 6,216,030 B1 * | 4/2001 | Howard et al. .............. 600/427 |
| 6,233,476 B1 * | 5/2001 | Strommer et al. .......... 600/424 |
| 6,272,370 B1 * | 8/2001 | Gillies et al. ................ 600/411 |
| 6,293,282 B1 | 9/2001 | Lemelson |
| 0,168,618 A1 | 11/2002 | Anderson et al. |
| 6,549,803 B1 | 4/2003 | Raghaven et al. |
| 7,266,227 B2 | 9/2007 | Pedain et al. |

FOREIGN PATENT DOCUMENTS

EP            0 702 966        3/1996

OTHER PUBLICATIONS

Furhang E.E. et al.; "A Monte Carlo Approach to Patient-specific Dosimetry"; Medical Physics, American Institute of Physics; New York, NY; Sep. 1996; pp. 1523-1529: XP000640764.*

(Continued)

*Primary Examiner*—Brian Casler
*Assistant Examiner*—Elmer Chao
(74) *Attorney, Agent, or Firm*—Renner, Otto, Boisselle & Sklar, LLP

(57) ABSTRACT

A method for identifying advantageous and non-advantageous infusion regions in the tissue includes capturing at least one of (i) functional anatomical data and (ii) structural anatomical data. The captured anatomical data is evaluated with computer assistance. Based on the evaluating step, the method includes determining infusion distribution information, such as directional and velocity information.

20 Claims, 1 Drawing Sheet

OTHER PUBLICATIONS

Office Action in connection with U.S. Appl. No. 10/075,108 dated Oct. 18, 2005.
Office Action in connection with U.S. Appl. No. 10/075,108 dated Mar. 30, 2006.
Office Action in connection with U.S. Appl. No. 10/075,108 dated Jun. 7, 2006.
Office Action in connection with U.S. Appl. No. 10/075,108 dated Aug. 25, 2006.

* cited by examiner

DETERMINING DISTRIBUTION FOR PLANNING AN INFUSION

RELATED APPLICATION DATA

This application claims priority of U.S. Provisional Application No. 60/437,368, filed on Dec. 31, 2002, which is incorporated herein by reference in its entirety.

PARTIES TO A JOINT RESEARCH AGREEMENT

BrainLAB AG, a German corporation, and Image-Guided Neurologics Inc., a U.S. corporation, are parties to a Joint Research Agreement.

FIELD OF THE INVENTION

The invention relates generally to the field of planning an infusion and, more particularly to a method for identifying advantageous and/or non-advantageous infusion regions as well as a method and a device for assisting planning for introducing an infusion fluid.

BACKGROUND OF THE INVENTION

Various medical methods require therapeutic agents to be directly infused into the tissue, with the aim of achieving a broad and optimum homogeneity of the distribution of the infusion fluid in the tissue. While the administered agents are generally fluids, the term "infusion" can include the administering of, for example, any fluid or gaseous or solid substance or infusion agent, such as, for example, medicines, cells, genes, enzymes, proteins, antibodies, hormones, viruses or the like. These substances are generally introduced directly into a body or body tissue, for example, into a patient's brain. The substance can be supplied within a relatively short period of time, e.g., by injection, or over a longer period of time, e.g., at a continuous, or, as the case may be, variable supply rate of the substance.

A method and a device for the targeted release of a medicine using magnetic resonance image detection are known from U.S. Pat. No. 6,061,587. U.S. Pat. No. 5,583,902 discloses a method and a device for predicting organ-specific contrast amplification in a patient before an injection. U.S. Pat. No. 5,720,720 discloses a method for micro-infusing at high flow rates, enabling agents to be released into the brain and other fixed tissue structures with convection-amplification. U.S. Pat. No. 5,205,289 describes an optimized dosage administering system using graphic simulation techniques and computer-assisted, numerical optimization. U.S. Pat. No. 3,690,318 discloses a fluid infusion device comprising variable flow regulating means. A method and a device for nuclear spin flow image detection are known from U.S. Pat. No. 5,195,524. U.S. Pat. No. 5,840,026 describes a contrast medium supply system, which starts setting the contrast medium concentration and the injection parameters before or during an injection.

The homogeneity of the distribution of an infusion or of an infusion fluid can deteriorate if the infusion agent is introduced into a region in which the agent is transported through directional channels, which are not in themselves the infusion target, nor their end points. Instead of diffusing into the actual target areas, the infusion agent runs off along these "tracks", without achieving the desired effect.

SUMMARY OF THE INVENTION

It is an object of the present invention to achieve increased control over the distribution of the infusion agent. One object of the invention is to prevent the infusion insertion point from coming too near to directional channels in which the infusion agent is quickly transported away and thus runs off without any effect.

According to one aspect of the invention, the invention is directed to a method for identifying advantageous and/or non-advantageous infusion regions in a tissue. Functional and/or structural anatomical data can be captured and the anatomical data can be evaluated with computer assistance. The anatomical data can be evaluated with respect to the distribution information contained therein, such as directional and/or velocity information. This can be used, for example, to identify, before the infusion fluid is introduced, the directional channels at which infusion fluid may be expected to be rapidly transported away when it is introduced. The basis for this is formed by anatomical data such as can be determined, for example, by an imaging system, such as a nuclear spin tomograph, a computer tomograph or similar known imaging systems. In this way, it is possible both to capture structural anatomical data, i.e., only data on the tissue structure, and to obtain functional information, for example, data on certain regions having a specific function (auditory cortex, visual cortex, etc.) in the brain.

Using this information, it is then possible with computer assistance to determine which regions of the tissue contain transport pathways. In this way, it is also possible to find out whether the infusion agent will run off along so-called "tracks" without any effect if it is introduced at a particular point, or whether there will be a homogeneous diffusion into the surrounding tissue. It is therefore possible in this way, even before performing an infusion, to distinguish target areas having advantageous distribution properties from those having less advantageous or non-advantageous distribution properties.

The structural and/or anatomical properties of the tissue can change during the infusion. Such change can result from the physical and/or biochemical conditions of the infusion itself or from a reaction between the infused material and the tissue. In order to take these changes into account in their chronological course, corresponding adjustments can be made to the distribution information and made available to the user.

In one embodiment, the method for identifying transport pathways is based on diffusion measurements. These measurements can be modified in a mathematical algorithm by forming mean values of interference signals and converted into direction-independent (modified) or direction-dependent velocity information per volume element. Representations of the isotropy and/or anisotropy can likewise be based on diffusion measurements and can contain information on the direction-dependence of the fluid-transparency (permeability) of a volume element. The velocity information and isotropy information can be further used, each alone or combined with each other. Furthermore, the velocity information and/or isotropy information can be combined with other anatomical data, to increase or specify its significance.

In one embodiment, the velocity of diffusion of a volume element in the tissue can be determined within the framework of evaluating the distribution information, such as, for example, by identifying regions having rapid diffusion.

The distribution information, such as the diffusion velocity and isotropy, can be determined two-dimensionally, i.e., on the basis of two-dimensional image information. If a number of such two-dimensional image information data sets are available on the anatomical structure, which in their planes make information on the distribution of the infusion fluid accessible, then these two-dimensional data sets can be combined to obtain three-dimensional distribution information. Alternatively, there exists the possibility of directly determining three-dimensional image data sets and evaluating them with respect to their distribution information.

In accordance with another aspect, the invention relates to a method for assisting planning for introducing an infusion fluid into regions of the brain, wherein infusion regions are identified using a method such as been described above. Furthermore, introducing the infusion at a selected point is also planned and/or carried out by means of medical, e.g., stereotactic navigation. The person positioning the infusion can then be shown, with the aid of medical navigation, where the target of the infusion device is supposed to be. While positioning the infusion he can be guided in shifting the same until the optimum introduction target is reached. The infusion instruments can be tracked by a camera system, or magnetically by known tracking methods, and their spatial location can be shown in relation to the patient's anatomy on an image output.

It is possible within the framework of the aforementioned method to combine anatomical, functional and/or structural tissue data with information on the distribution of the infusion fluid to be expected. In other words, the anatomical patient data determined for simulating the distribution can also be used during navigation by being referenced and/or registered in the navigation system.

In accordance with another aspect, the present invention relates to a device for assisting planning for introducing an infusion fluid into regions of the brain. The device can include an imaging device, such as a nuclear spin tomograph, for capturing functional and/or structural anatomical data. A computer which, on the basis of the captured anatomical data, can produce an evaluation of the distribution information of an infusion fluid when it is introduced at particular points. The device can include computer-assisted, medical planning and navigation system for assisting in positioning an infusion device. Evaluating the distribution information and navigating can be assisted by a single computer system or by separate computer systems. Such a device enables the present invention to be performed and adapted, with the aforementioned advantages with respect to the distribution of the infusion agent.

The imaging device, the computer or computers and the navigation system can be connected to each other via data connections, for a constant or retrievable exchange of data. It is possible to connect individual devices or all of these devices to each other in this way.

Furthermore, the invention also relates to a program which, when run on a computer or loaded onto a computer, causes the computer to perform a method as described above, and to a computer program storage medium comprising such a program.

BRIEF DESCRIPTION OF DRAWINGS

These and further features of the present invention will be apparent with reference to the following description and drawings, wherein.

DETAILED DESCRIPTION OF THE INVENTION

Figure 1:
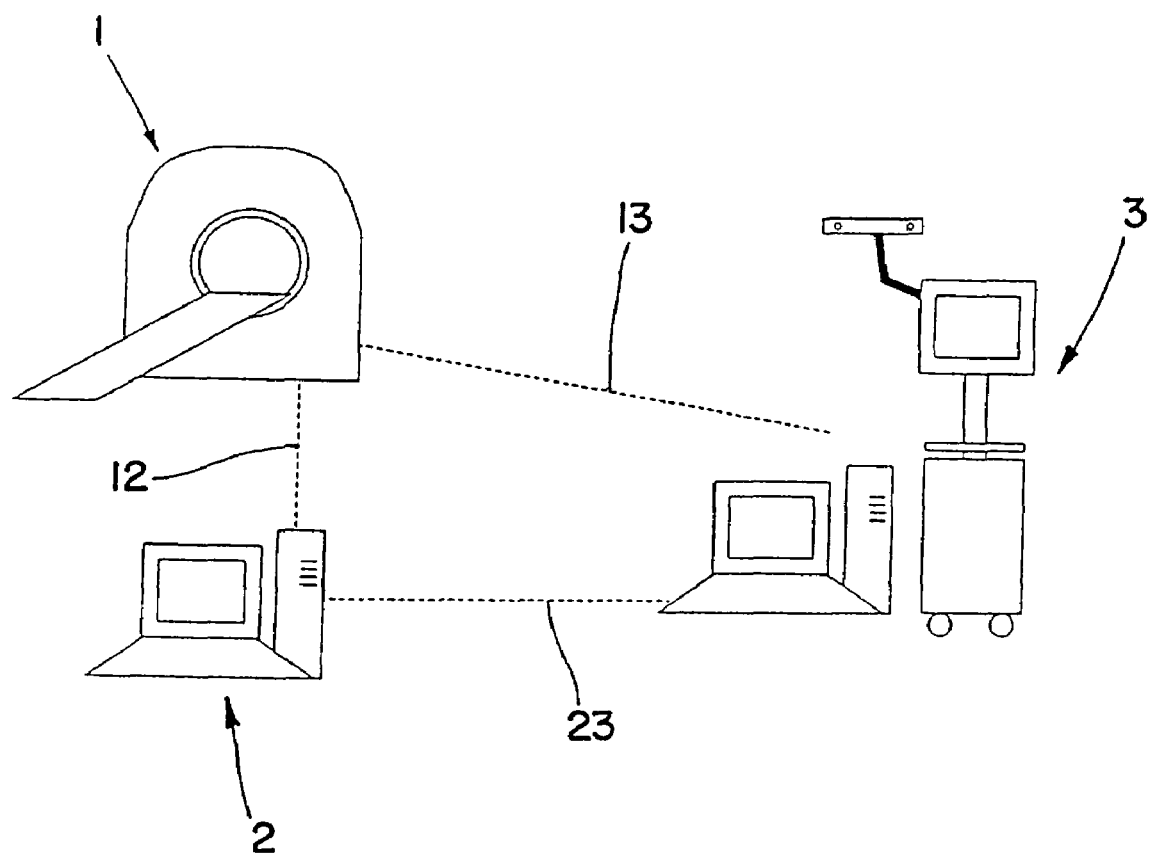
FIG. 1 is a diagrammatic illustration of a system for identifying advantageous and non-advantageous infusion regions and/or for assisting planning for introducing a fluid in accordance with the present invention.

It is to be appreciated that the term "infusion", as used herein is intended to include the administering of, for example, any fluid or gaseous or solid substance or infusion agent, such as for example medicines, cells, genes, enzymes, proteins, antibodies, hormones, viruses or the like.

With reference to FIG. 1, a device or system for identifying advantageous and non-advantageous infusion regions and/or for assisting planning for introducing a fluid is provided. The system includes an imaging device 1, such as a nuclear spin tomograph with a patient couch. A patient can be introduced into the nuclear spin tomograph, for example, via the head, and structural and/or functional anatomical data can be captured. The captured structural and/or functional anatomical data can be used to determine the structure of the head, for example, the brain. Once the recorded images have been processed, which can simply be performed in a processor in the nuclear spin tomograph, information is then available on the structure of the patient's brain. In one embodiment, this data is recorded in such a way that brain structure can be registered and/or referenced in a medical navigation system, such as is indicated by the reference numeral 3. The medical navigation system can include an optical navigation system, such as is described in co-owned U.S. Pat. No. 6,351,659, which is incorporated herein by reference in its entirety.

In this embodiment, before the nuclear spin tomograph is recorded, markings can be attached to the patient's head. These markings can be identified both in the nuclear spin images and when tracked using the navigation system, such that the positional relationship between the markings and the detected regions of the brain structure is established and can also be used later in the course of the navigated positioning of the infusion.

A data connection 13 can be provided for exchanging data between the nuclear spin tomograph 1 and the navigation system 3. The data connection can include, for example, a data line, radio data transmission, or data transmission via transfer by storage media. The connection can thus be an on-line (continuous) connection, but can also be a retrievable (off-line) connection.

A processor or computer system 2 can exchange data with the nuclear spin tomograph 1 via an on-line or off-line connection 12. The functional and/or structural anatomical data from the nuclear spin tomograph 1, determined as described above, can be communicated to the computer 2 via the line 12. A program can then start in the computer, which on the basis of said anatomical data, evaluates and/or displays the distribution information and/or simulates the distribution of an infusion fluid at particular points. This will reveal that at some points, at which directional and/or rapid channels (tracks) are present, there can be a non-advantageous distribution, i.e., rapid run-off into undesired areas, if these are selected as the infusion point. On the other hand, target points for the infusion can be identified, at which a homogenous distribution of the infusion fluid may be expected. The computer 2 can make the advantageous points distinguishable from the non-advantageous ones, for example, by inserting corresponding indicators in the image data sets produced.

Using this information on advantageous and non-advantageous infusion regions in the brain tissue, one or more positions for the infusion device can then be planned by the user, such that a maximally homogenous distribution of the infusion fluid may be expected. To this end, the user of the computer 2 inputs the desired positions for the infusion device with the aid of a user interface and taking into account the information presented to him on the computer 2. With the aid of the distribution information contained in the computer, advantageous target points for the positions of the infusion device can also be suggested by the computer. Once this procedure has been concluded, the computer 2 transfers the positions for the infusion devices and/or other information to the navigation system 3 via an interface 23.

In addition to the navigation system described and incorporated above, the navigation system can be a known optical navigation system, such as is, for example, described in DE 196 396 152, the disclosure of which is incorporated herein its entirety by reference. Such a navigation system 3, which positionally tracks and registers the patient and medical instruments, for example, the infusion device, and displays them on an image output, referenced to determined image data, is shown in the drawing as an optical, camera-assisted system. Other navigation systems, including but not limited to magnetic or inductive navigation systems based on tracking magnetic and/or inductive signal emitters in the magnetic and/or electrical fields may be used.

When positioning the infusion, the navigation system 3 is placed near the patient or the patient is moved to it. The navigation system 3, which benefits from the anatomical data of the patient communicated via the line 12 and/or 23, can spatially assign this anatomy. This is due to the fact that the patient is wearing corresponding markings and/or natural landmarks, which have been both positionally recorded by the nuclear spin tomograph 1 and can be positionally detected by the navigation system using its camera system. Furthermore, the navigation system 3 can positionally track an infusion device provided with corresponding markings, and incorporate it such that it is clear to the person carrying out the treatment where the tip of the infusion device is currently situated with respect to the patient's anatomy. The navigation system 3 obtains the third piece of information required, i.e., the data on advantageous and/or non-advantageous infusion regions in the tissue, from the computer 2 via the data line 23. With the aid of this data, specific regions in the brain, which are or are not advantageous for the infusion insertion point can be distinguished. When positioning the infusion, it can then be shown on a two-dimensional or three-dimensional view on the image output of the navigation system 2 where the tip of the infusion device is currently situated and whether this point promises a homogeneous distribution of the infusion fluid or not. When a physician recognizes on the screen output that he has just reached an advantageous infusion region with the tip of his instrument, the instrument can be placed there.

Accordingly, a method and a device which prevent infusion openings for infusion devices from being placed at unsuitable points in the tissue for releasing the infusion fluid are provided. This provides increased control over the effectiveness of the distribution of the infusion agent. The agent can, for example, be highly effectively injected directly into particular tumors. Because the infusion agent is prevented from running off without any effect, it is possible to use smaller quantities of the infusion agent and, because of the enabled homogeneous distribution, to generate an optimum effect. Furthermore, other regions of the brain and/or the body as a whole are prevented from being damaged by infusion fluid running off in an uncontrolled manner.

Although particular embodiments of the invention have been described in detail, it is understood that the invention is not limited correspondingly in scope, but includes all changes, modifications and equivalents coming within the spirit and terms of the claims appended hereto.

What is claimed is:

1. A method for planning the introduction of a fluid in a tissue, the method comprising:
    capturing via an imaging system functional anatomical data and/or structural anatomical data before infusion of a fluid into the tissue;
    evaluating the captured functional and/or structural anatomical data with computer assistance and without use of an infusion fluid;
    based on the evaluating step, identifying directional channels within the tissue and determining infusion distribution information related to the identified directional channels, the identified directional channels and/or infusion distribution information being indicative of advantageous and/or non-advantageous infusion regions;
    presenting identified advantageous and/or non-advantageous infusion regions for viewing by a user; and
    based on the advantageous and/or non-advantageous infusion regions, using medical navigation to introduce an infusion device at a selected point.

2. The method as set forth in claim 1, wherein evaluating the captured functional and/or structural anatomical data includes simulating apart from the tissue a distribution of an infusion at a plurality of regions in the tissue.

3. The method as set forth in claim 1, wherein the determined infusion distribution information includes direction information and/or velocity information relating to infusion regions in the tissue.

4. The method as set forth in claim 3, further comprising: identifying regions of rapid diffusion.

5. The method as set forth in claim 3, further comprising: determining isotropy and an isotropy of flow directions in the regions in the tissue.

6. The method as set forth in claim 1, wherein the functional and/or structural anatomical data is evaluated two-dimensionally with respect to the distribution information which it contains.

7. The method as set forth in claim 1, wherein the functional and/or structural anatomical data is evaluated three-dimensionally with respect to the distribution information which it contains.

8. The method as set forth in claim 1, further comprising:
    evaluating the functional and/or structural anatomical data over a period of time with respect to the distribution information; and
    making adjustments in the distribution information, said adjustments being responsive to anatomical or structural conditions which have changed over the period of time.

9. The method as set forth in claim 1, further comprising: calculating a distribution volume for an infusion fluid from the functional and/or structural anatomical data.

10. The method as set forth in claim 1, wherein the functional and/or structural anatomical data is captured two-dimensionally.

11. The method as set forth in claim 10, wherein a number of two-dimensional data sets on the functional and/or structural anatomical data are combined to obtain three-dimensional information.

12. The method as set forth in claim 1, wherein the functional and/or structural anatomical data is captured three-dimensionally.

13. The method as set forth in claim 1, further comprising obtaining diffusion measurements before infusion via magnetic resonance diffusion imaging and identifying transport pathways based on the diffusion measurements.

14. A method for assisting planning for introducing an infusion fluid into regions of a brain, said method comprising:
    identifying infusion regions said identifying including:
    capturing via an imaging system functional anatomical data and/or structural anatomical data before infusion of a fluid into the tissue;

evaluating the captured functional and/or structural anatomical data with computer assistance and without use of an infusion fluid;

based on the evaluating step, identifying directional channels within the tissue and determining infusion distribution information related to the identified directional channels, the identified directional channels and/or infusion distribution information being indicative of advantageous and/or non-advantageous infusion regions;

presenting identified advantageous and/or non-advantageous infusion regions for viewing by a user;

based on the advantageous and/or non-advantageous infusion regions, using medical navigation to introduce an infusion device at a selected point; and wherein introducing the infusion at a selected point is planned using stereotactic planning.

15. The method as set forth in claim 14, wherein anatomical, functional and/or structural tissue data are combined with information on a distribution of the infusion fluid to be expected for planning or navigation.

16. A method for assisting navigation for introducing an infusion into regions of a brain, said method comprising:

identifying the infusion regions and positions for an infusion device said identifying including:

capturing via an imaging system functional anatomical data and/or structural anatomical data before infusion of a fluid into the tissue;

evaluating the captured functional and/or structural anatomical data with computer assistance and without use of an infusion fluid;

based on the evaluating step, identifying directional channels within the tissue and determining infusion distribution information related to the identified directional channels, the identified directional channels and/or infusion distribution information being indicative of advantageous and/or non-advantageous infusion regions;

presenting identified advantageous and/or non-advantageous infusion regions for viewing by a user;

based on the advantageous and/or non-advantageous infusion regions, using medical navigation to introduce an infusion device at a selected point; and wherein introducing the infusion device at a selected point is planned using stereotactic navigation.

17. A device for assisting planning for introducing an infusion fluid into regions of the brain, said device comprising:

an imaging device that captures functional and/or structural anatomical data before an infusion of fluid into regions of the brain;

a processor which is programmed to:

perform and assist in evaluating the functional and/or structural anatomical data in order to identify directional channels within the regions of the brain and determine infusion distribution information related to the identified directional channels, the directional channels and infusion distribution information being indicative of advantageous and non-advantageous infusion regions;

produce and evaluate a distribution simulation apart from the regions of the brain before the infusion fluid is infused, the distribution simulation being indicative of an infusion fluid when it is introduced at particular points, on the basis of the captured anatomical data; and a computer-assisted, medical planning and navigation system for assisting in positioning an infusion device.

18. The device as set forth in claim 17, wherein the imaging device includes a nuclear spin tomograph.

19. The device as set forth in claim 17, wherein the imaging device, the processor and the medical planning and navigation system are connected to each other via data connections, thereby providing a constant or retrievable exchange of data.

20. A method for planning the introduction of a fluid in a tissue, the method comprising:

capturing via an imaging system functional anatomical data and/or structural anatomical data before infusion of any infusion fluid into the tissue;

evaluating the captured functional and/or structural anatomical data with computer assistance;

based on the evaluating step, identifying directional channels within the tissue and determining infusion distribution information related to the identified directional channels, the identified directional channels and/or infusion distribution information being indicative of advantageous and/or non-advantageous infusion regions; and presenting identified advantageous and/or non-advantageous infusion regions for viewing by a user; and based on the advantageous and/or non-advantageous infusion regions, using medical navigation to introduce an infusion device at a selected point.

* * * * *